United States Patent [19]

Homann et al.

[11] Patent Number: 4,695,661

[45] Date of Patent: Sep. 22, 1987

[54] CATALYTIC SYSTEM AND A PROCESS FOR PREPARING ALPHA, OMEGA-$C_4$ THROUGH $C_{20}$ ALKENOLS

[75] Inventors: Walter K. Homann, Duelmen; Lothar Fischer, Marl, both of Fed. Rep. of Germany

[73] Assignee: Huls Aktiengesellschaft, Marl, Fed. Rep. of Germany

[21] Appl. No.: 841,490

[22] Filed: Mar. 19, 1986

[30] Foreign Application Priority Data

Mar. 23, 1985 [DE] Fed. Rep. of Germany ....... 3510568

[51] Int. Cl.$^4$ ..................... C07C 29/60; C07C 33/025
[52] U.S. Cl. ..................................... 568/903; 502/208
[58] Field of Search .......................................... 568/903

[56] References Cited

U.S. PATENT DOCUMENTS 3,862,964  1/1975  Weisang et al. ..................... 568/903
3,957,900  5/1976  Weisang et al. ..................... 568/903
4,250,343  2/1981  Kaufhold et al. ................... 568/903

FOREIGN PATENT DOCUMENTS 1149281  4/1969  United Kingdom ................ 568/903
 156948  5/1962  U.S.S.R. .............................. 568/903

Primary Examiner—J. E. Evans
Attorney, Agent, or Firm—Quaintance, Murphy & Presta

[57] ABSTRACT

In order to produce pure alpha, omega-$C_4$ to $C_{20}$ alkenols having purities in excess of 90% by dehydrating the corresponding alpha, omega-$C_4$ to $C_{20}$ diols, a catalyst is used which was prepared by using an alkaline earth orthophosphate or alkaline earth hydrogen phosphate or by reacting an alkaline earth compound with phosphoric acid into the corresponding phosphate and then adding an alkali or alkaline earth compound. This catalyst is suitable to be shaped, next it is dried and then calcined at temperatures between 350° and 950° C. The educt dehydration takes place at temperatures between 300° and 500° C. in selective and partial manner to obtain pure alpha, omega-$C_4$ to $C_{20}$ alkenols at conversions exceeding 90%.

14 Claims, 8 Drawing Figures

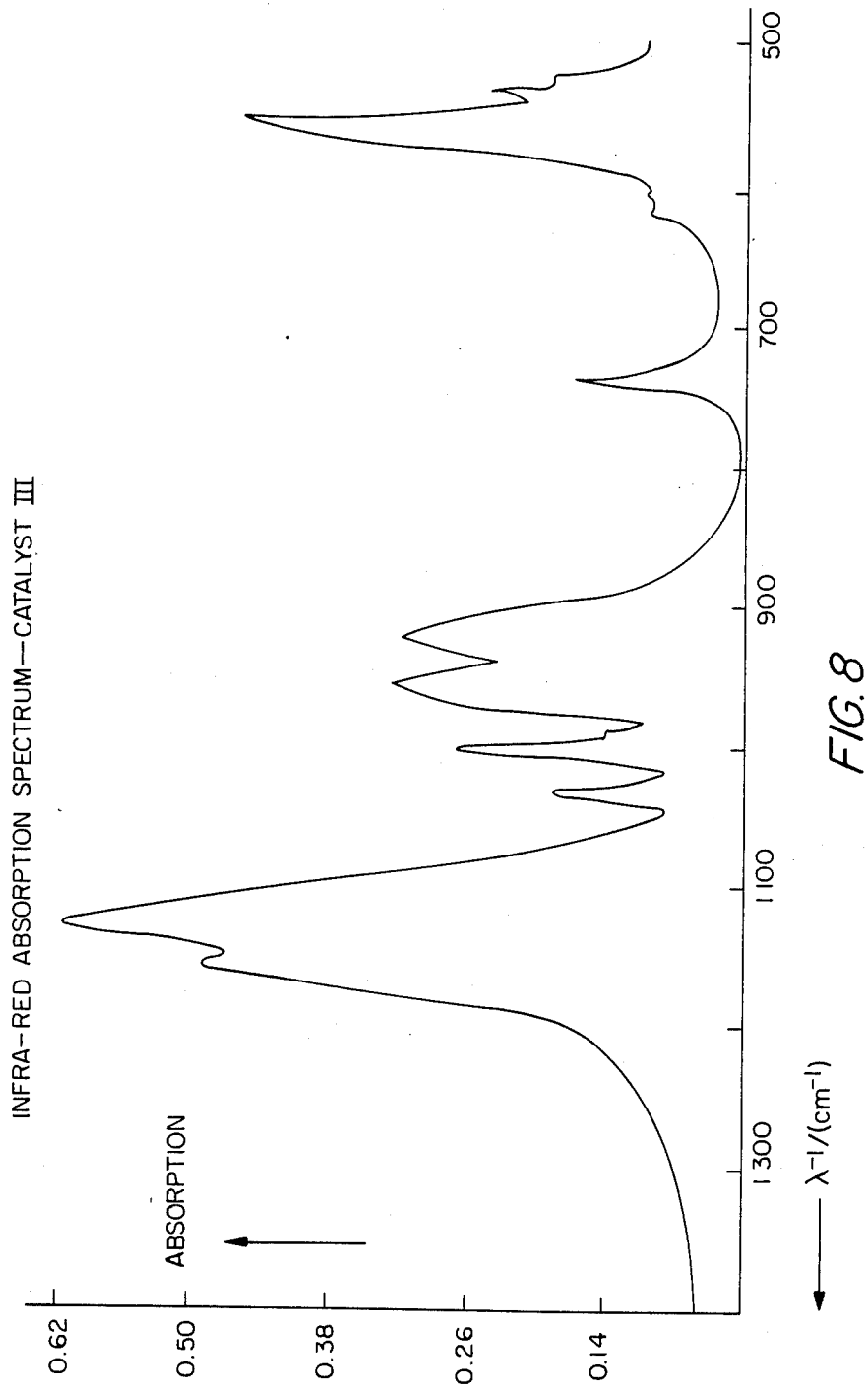

CATALYTIC SYSTEM AND A PROCESS FOR PREPARING ALPHA, OMEGA-$C_4$ THROUGH $C_{20}$ ALKENOLS

CROSS-REFERENCE TO A RELATED APPLICATION

Applicants claim priority under 35 USC 119 for application P No. 35 105 68.2, filed Mar. 23, 1985, in the Patent Office of the Federal Republic of Germany.

BACKGROUND OF THE INVENTION

The field of the present invention is catalytic systems.

The invention is particularly concerned with synthesizing alpha, omega-$C_4$ through $C_{20}$ alkenols having purities in excess of 85%.

The state of the art of the preparation of pure alpha, omega-$C_6$ to $C_{20}$-alkenols may be ascertained by reference to British Pat. Nos. 1,355,704 and 1,355,705 and U.S. Pat. No. 4,250,343, the disclosures of which are incorporated herein by reference.

In order to synthesize alpha, omega-$C_4$ through $C_{20}$ alkenols with purities in excess of 85% by catalytically dehydrating the corresponding alpha, omega-$C_4$ through $C_{20}$ diols, neutral, simple, or mixed pyrophosphates of lithium, sodium, strontium or barium or mixtures of these compounds are employed as catalysts in the method of U.S. Pat. No. 4,250,343. This method suffers from the drawback on the one hand that there is formation of significant proportions of alkanols and, on the other hand, that the formation of other by-products increases sensibly when the conversions exceed 80% and appreciably when they are beyond 90% as disclosed at column 3, lines 63 through 65 of U.S. Pat. No. 4,250,343. Accordingly, there is a need to find a process which, besides the reduction in the alkanol content also exhibits an adequately high selectivity at conversion in excess of 90%.

SUMMARY OF THE INVENTION

This need is met by a process for preparing pure alpha, omega-$C_4$ to $C_{20}$ alkenols having purities in excess of 90% by the catalytic dehydration of the corresponding alpha, omega-$C_4$ to $C_{20}$ diols, wherein a catalytic substance is prepared by using alkaline earth metal orthophosphate or alkaline earth metal hydrogen phosphate or by reacting an alkaline earth metal compound with phosphoric acid to form a corresponding phosphate and adding an alkali metal compound or an alkaline earth metal compound, this catalytic substance then possibly being shaped and dried, whereupon it is calcined at temperatures between 350° and 950° C. The alpha, omega-$C_4$ to $C_{20}$ diols are dehydrated at temperatures of 300° to 500° C. selectively and partly into alpha, omega-$C_4$ to $C_{20}$ alkenols with purities in excess of 90% at conversions in excess of 90% using simple or mixed phosphates of the elements of group IIA of the periodic table of elements doped with alkali or alkaline earth metal compounds as the catalysts.

BRIEF DESCRIPTION OF THE DRAWINGS

The appended drawings illustrate plots of the data obtained in the specific examples of the present invention, wherein:

FIG. 8 is a plot of the infra-red absorption spectrum of Catalyst III.

DESCRIPTION OF THE PREFERRED EMBODIMENTS

Figure 1:
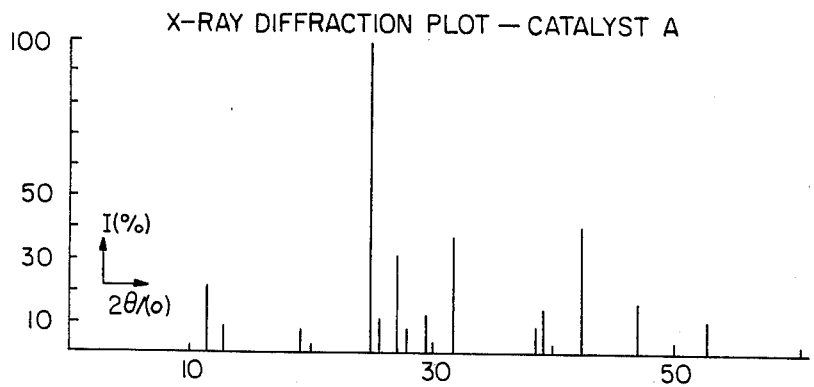
FIG. 1 is the X-ray diffraction plot of Catalyst A.

Surprisingly the catalysts of the present invention prepared illustratively as indicated by the Specific Examples and contrary to the disclosure of U.S. Pat. No. 4,250,343 exhibit high selectivities also at conversions higher than 90%. This permits a more economical production with purities above 90%. Thus, the alkanol proportion is merely 0.3 to 4.5%, preferably 0.5 to 2.5% in the crude output with a simultaneous diolefin content of 0.3 to 7.0%, preferably from 0.5 to 5%. Additionally, the catalyst system of the present invention achieves substantially longer service life in excess of 5 months, without significant losses in activity and selectivity having been found. This could not have been expected having in mind the disclosure in Chem. Abstr. 58 (1963), p 2353, that tricalcium phosphate treated with a basic compound such as sodium hydroxide requires regeneration as a dehydration catalyst after 100 hours due to its strong drop in activity.

Alkali and alkaline earth metal compounds are suitable as additives, illustratively the oxides, hydroxides, carbonates or phosphates of the metals of Group IA of the periodic table and/or of Group IIA of the periodic table such as of beryllium, magnesium, calcium and/or strontium. Preferably the phosphates are used in the form of diphosphates, especially those of sodium. Preferably again the additives are introduced in proportions of 2 to 25%, especially 5 to 15% by weight, calculated as metal oxides and referred to the main component (calculated as metal oxide).

Simple or mixed phosphates of the elements of Group IIA are used as the main catalyst component, illustratively barium orthophosphate and barium hydrogen phosphate. Preferably the barium compounds are used. Obviously oxides, hydroxides or salts such as barium carbonates can also be reacted with phosphoric acid and the reaction product can be employed as the main component. These phosphates are activiated by additives.

The catalysts of the state of the art as disclosed in British Pat. Nos. 1,355,704 and 1,355,705; and U.S. Pat. No. 4,250,343 are prepared by precipitation from aqueous solutions, for instance sodium diphosphate with barium nitrate. However, this manufacturing procedure requires handling large volumes of solutions, mother liquors and rinse waters which must be cleaned requiring high technological and industrial expense before being discharged as waste waters without ecological damage. Additionally, it is difficult to set the sodium content in the catalyst preparation by precipitation.

The present modification of the preparation for a reaction between an alkaline earth metal compound such as barium carbonate and phosphoric acid with an ensuing specified addition of alkali or alkaline earth metal compound such as sodium diphosphate offers a substantial improvement, wherein the addition of the sodium diphosphate is mandatory at a low dosing rate to obtain at once a shapable material.

Following calcining between 350° and 950° C. the water separation from a previously formed barium hydrogen phosphate is supposed to determine the formation of barium diphosphate in addition to the sodium diphosphate. However, the x-ray diffraction plot shows reflections which do not correspond to the JCPDS catalogue for barium diphosphate. On the other hand there are infra-red absorption bands compatible with a diphosphate structure.

The most active and the most selective catalysts were obtained according to the present invention when the alkaline earth metal phosphate, or, as discussed above, after a complete reaction of the alkaline earth carbonate with phosphoric acid, the alkali or the alkaline earth metal compound such as sodium diphosphate is admixed at a low dosing rate. Illustratively the dosing rate is 5 grams/hour to 20 grams/hour when employing 1 to 10 kg barium carbonate so that the reaction temperature does not exceed 30° C. The catalyst so obtained following calcining at 350° to 950° C. is characterized by its infra-red absorption spectrum in that at 700 to 720 $cm^{-1}$, at 750 $cm^{-1}$, and at 1,110 $cm^{-1}$ only weak bands or no bands at all appear and that very strong bands are present at 920 to 924 $cm^{-1}$ and at 1,126 to 1,130 $cm^{-1}$.

The catalytic systems of the present invention are prepared, for example, by reacting barium carbonate with ortho-phosphoric acid and by then adding the required amount of additive. The substance so obtained is dried, extruded and calcined at 350° C. to 950° C., preferably at 400° C. to 600° C.

Examples of the catalysts of the present invention include: the reaction product of barium carbonate and phosphoric acid doped with 10–50% by weight tetrasodiumdiphosphate, tetrapotassiumdiphosphate or tetracesiumdiphosphate.

This procedure is also described comprehensively in the Examples below.

The structures of the catalysts of the invention are still unknown.

The infra-red absorption spectra and the x-ray diffraction plots of catalysts II and III, for instance, deviate from those of the diphosphates (Examples 2b and 3b). Therefore, in view of the preparation and also as shown by the infra-red spectra and the x-ray diffraction plots, this is a catalyst different from the one defined in U.S. Pat. No. 4,250,343 (di- and pyrophosphate catalysts respectively).

The dehydration of the educts takes place at temperatures between 300° and 500° C., preferably at 350° to 450° C. As a rule standard pressure is used, though reduced or excess pressure can also be employed. Preferably the reaction is carried out continuously though the discontinuous mode also is possible.

It is recommended, in order to increase the selectivity, that the educt be mixed with inert substances such as nitrogen, noble gases or steam in the reaction or mixing zone. An increase in catalyst service life is simultaneously achieved thereby. As a rule the inert substances are admixed in proportions of 1 to 90 percent molar, preferably between 25 and 60 percent molar.

In the process of the present invention, the alpha, omega alkenols are also obtained at conversions in excess of 90% with high selectivities (70 to 95%) and with high purity (more than 90%). The alpha, omega alkenols so obtained and containing 4 to 20 carbon atoms are valuable aromatics and intermediate products for numerous further industrial synthesises.

SPECIFIC EXAMPLES

COMPARISON EXAMPLE A1

Preparing the catalyst A (without activation by alkali or alkaline earth compounds).

Sulfide-free barium carbonate is reacted with aqueous phosphoric acid solution at about 40° C. in a kneader. The $BaHPO_4$ reaction product is rid of excess water until there is an extrudable mixture. This mixture is then extruded and thereupon calcined to 450° C.

Figure 2:
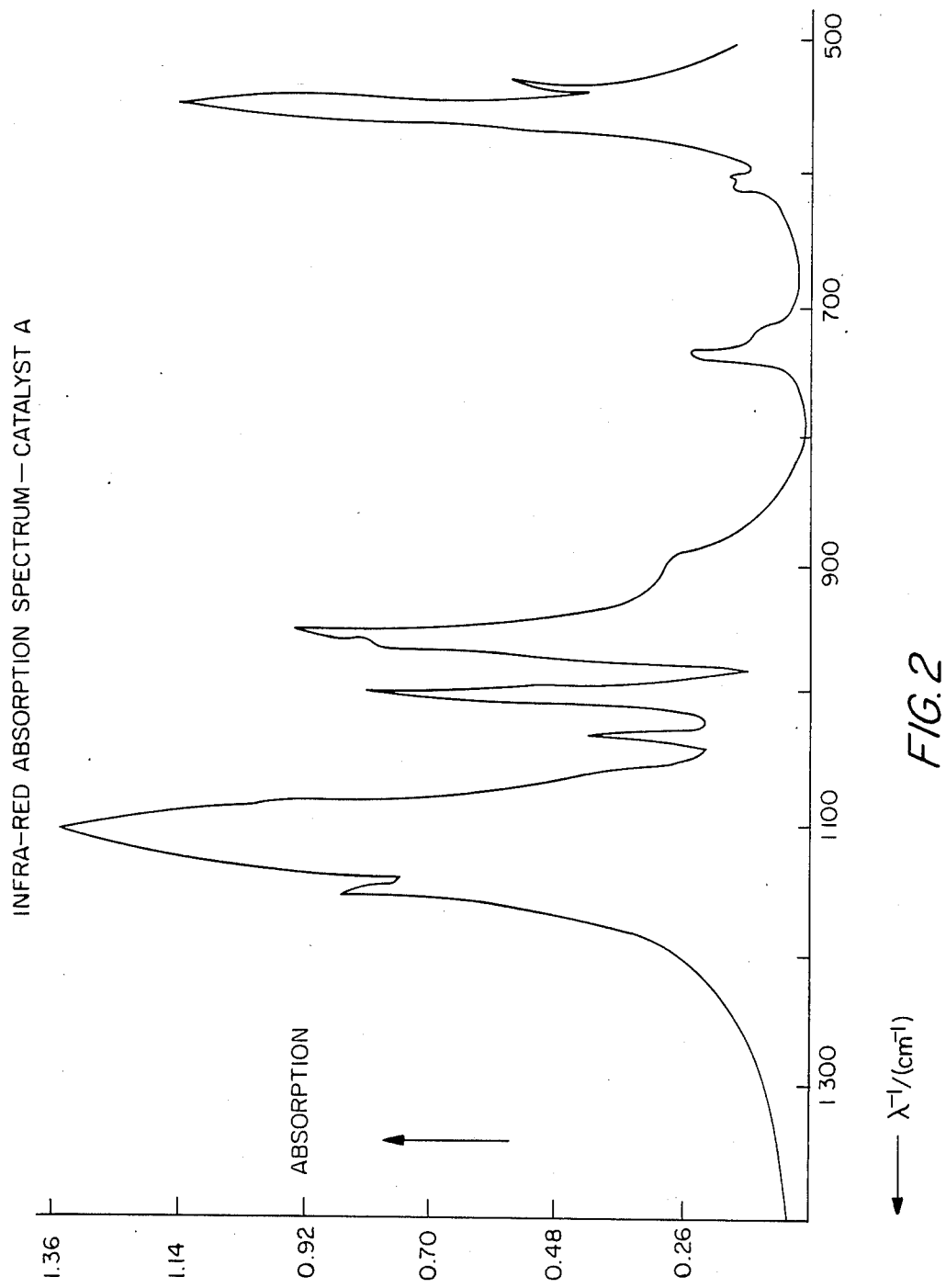
FIG. 2 is a plot of the infra-red absorption spectrum of Catalyst A.

4,000 g of sulfide-free barium carbonate (from Kali-Chemie Co.) are reacted at about 40° C. and at a high angular speed of the kneader arms with 2,348 g of aqueous 84.6% phosphoric acid solution in a time of 77 minutes. Kneading proceeds for 1 hour at 40° C. and then for about 0.5 hour at a product temperature of 60° C. Approximately, 5,250 grams of a substance are obtained which is extruded by a Hutt-Bepex machine into 4 mm strands. The extruded material is heated in a circulating air kiln at 110° C., the loss in mass incurred being about 8.7%. The dried strands then are heated in an airflow in a kiln from 110° to 450° C. over a period of time of about 2.2 hours and calcined, and further are kept 4 hours at this temperature. The mass loss is about 4.7%, the catalyst so obtained exhibiting the following properties:

| Chemical Composition: | |
|---|---|
| BaO content | 66.1% |
| SrO | 1.0 |
| $P_2O_5$ | 32.2 |
| $CO_2$ | 0.34 |
| $SO_3$ | 0.11 |
| Structure: | The x-ray diffraction plot of FIG. 1 does not clearly show that $Ba_2P_2O_7$ is present, the infra-red spectrum of FIG. 2 contains bands associated with $Ba_2P_2O_7$. |
| Physical Properties: | |
| Shape | strands |
| Diameter | 4 mm |
| Bulk Density | 1.69/$cm^3$ |
| Specific Pore Volume (total) | 0.16 $cm^3/g$ |
| ($D_p > 8$ nm) | 0.12 $cm^3/g$ |
| Specific Inner Surface $D_p > 8$ nm | 4.5 $m^2/g$ |

COMPARISON EXAMPLE B1

Preparing the Catalyst B

Figure 3:
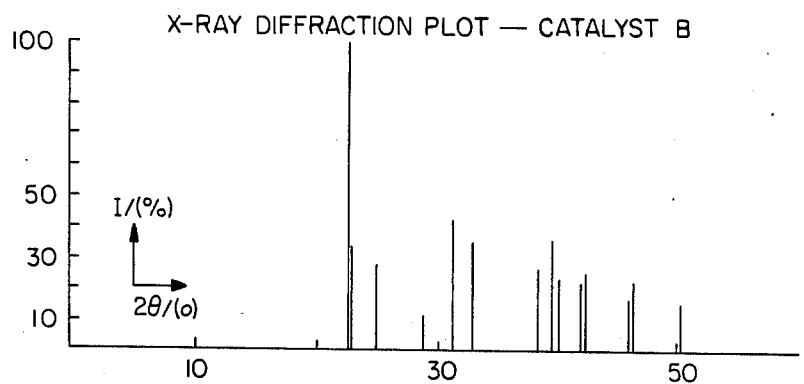
FIG. 3 is a plot of the X-ray diffraction of Catalyst B.
Figure 4:
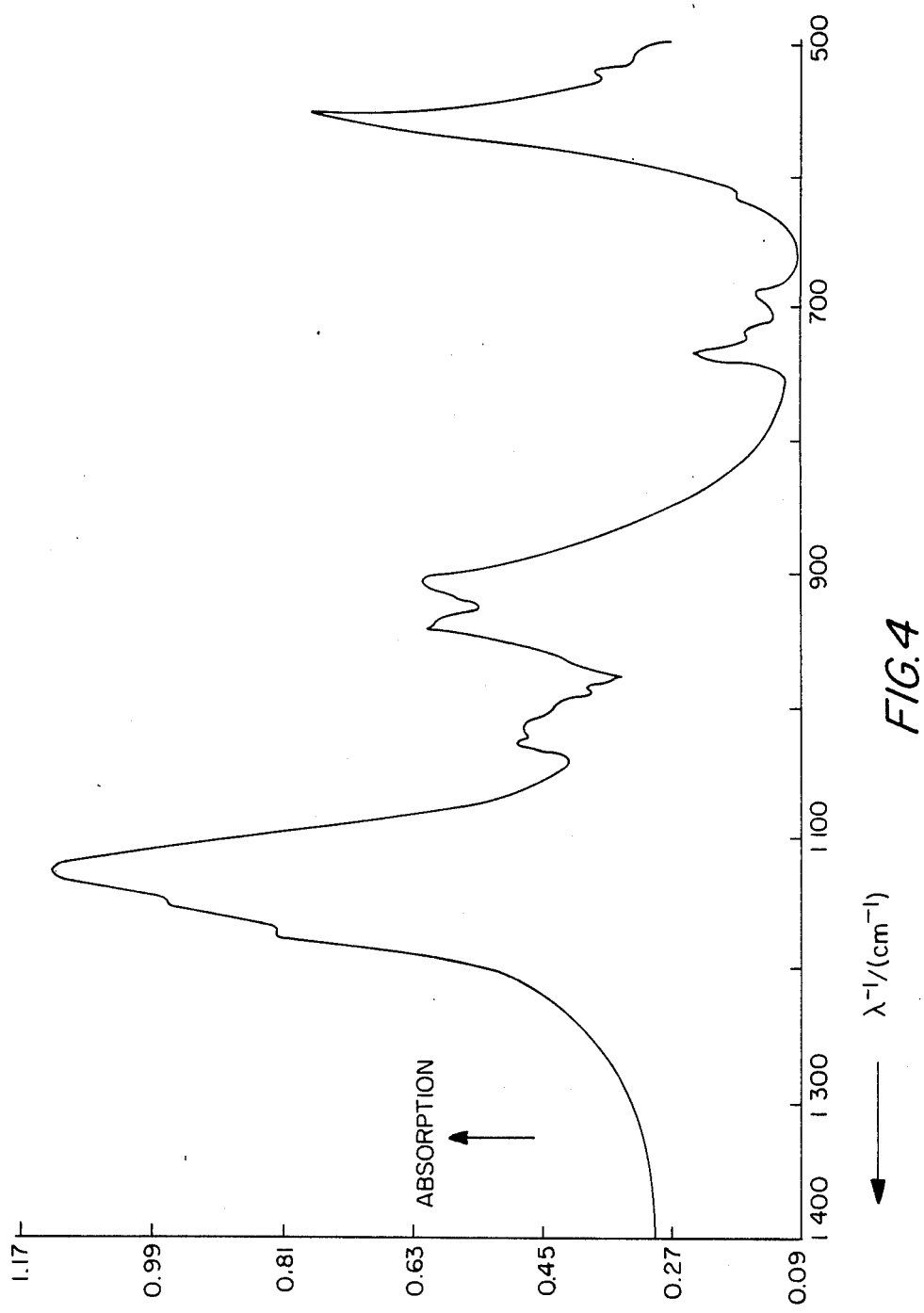
FIG. 4 is a plot of the infra-red absorption spectrum of Catalyst B.
Figure 6:
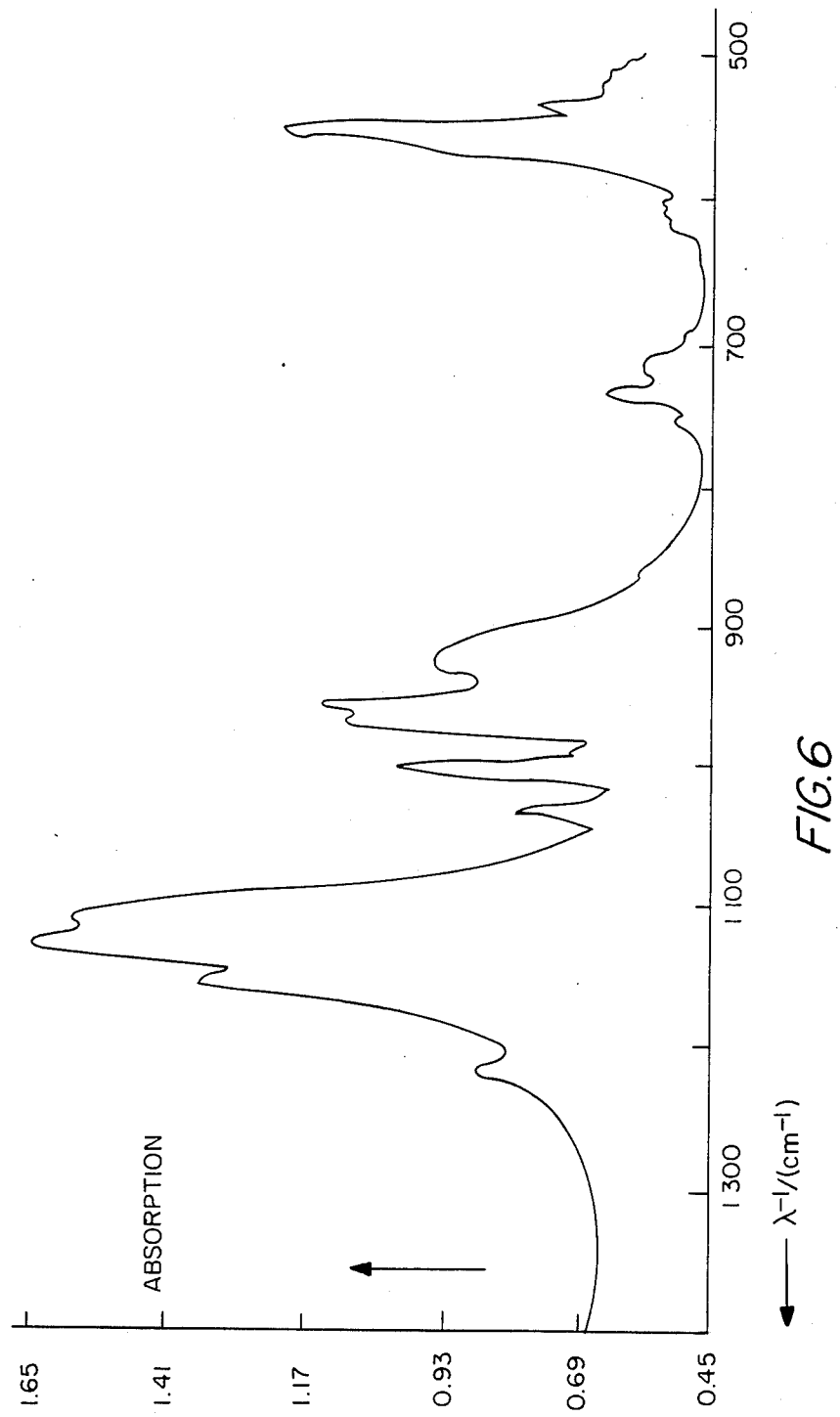
FIG. 6 is a plot of the infra-red absorption spectrum of Catalyst II.

A sample of the catalyst prepared according to Comparison Example A1 and dried at 110° C. next is treated at 950° C. for 1 hour in a retort furnace. Being sintered together, this sample then is comminuted and tested. The x-ray diffraction plot of this material in FIG. 3 is identical with the $Ba_2P_2O_7$ identified as No. 30-144 in the JCPDS catalogue. On the other hand, the infra-red absorption spectrum of FIG. 4 additionally contains further bands beyond those published by Watonabe et al, Bull. Chem. Soc. Jap. 56 (1983), p 3430, and the association of these further bands is unknown.

COMPARISON EXAMPLE C1

Preparing the control catalyst of British Pat. Nos. 1,355,704 and 1,355,705

By adding aqueous solutions of sodium diphosphate, barium diphosphate in aqueous solution is precipitated into barium nitrate. The supernatant liquid can be decanted, and the remainder can be filtered. The suspension also can be filtered as a whole. After partial drying of the substance, it is extruded. The strands are dried at 110° C. and calcined at 550° C.

The following solutions are then prepared:

1. An aqueous 22.78% $Na_4P_2O_7$ solution, by dissolving 88.5 kg (0.3328 mole) of water-free $Na_4P_2O_7$ in 300 kg of distilled water at 90° C.

2. An aqueous 11.42% $Ba(NO_3)_2$ solution, by dissolving 174 kg (0.6656 mole) of $Ba(NO_3)_2$ in 1350 kg of distilled water at 55° C.

The aqueous $Ba(NO_3)_2$ solution is added with stirring within 45 minutes to the $Na_4P_2O_7$ solution. Stirring proceeds for 3 hours. The temperature is about 50° C. and the pH value is 11.0.

The suspension is then filtered, the filter cake is dried, without prior washing, at 50° C. to a content of 30 ... 33% moisture.

Following comminution, the material is extruded into 6 mm strands which are dried in air at 110° C. and then are calcined at 550° C.

132 kg are obtained (88.4% of theoretical). The catalyst evinces the following properties:

| | |
|---|---|
| BaO content | 64.5% |
| $P_2O_5$ content | 31.2 |
| $Na_2O$ content | 3.6 |
| $NO_3$ content | <0.1 |
| Calcination loss (at 850° C.) | 0.1 |
| Shape: | strands |
| Diameter | 6 mm |
| Bulk Density | 1.23 g/cm$^3$ |
| Specific pore volume | 0.23 cm$^3$/g |
| Specific inside surface | 1.2 m$^2$/g. |

FIG. 1 for catalyst A is based upon the following data:

| $2\theta$ (°) | d (nm) | I (%) |
|---|---|---|
| 11.5 | 0.769 | 23 |
| 12.9 | 0.686 | 8 |
| 19.2 | 0.462 | 8 |
| 25.0 | 0.356 | 100 |
| 25.8 | 0.345 | 11 |
| 27.3 | 0.326 | 31 |
| 28.1 | 0.317 | 9 |
| 29.6 | 0.302 | 14 |
| 31.8 | 0.281 | 38 |
| 38.8 | 0.232 | 8 |
| 39.2 | 0.230 | 15 |
| 42.4 | 0.213 | 40 |
| 47.0 | 0.193 | 17 |
| 52.8 | 0.173 | 9 |

Wherein:
$\theta$: angle of diffraction
d: lattice plane distance
I: intensity

FIG. 3 for catalyst B is based upon the following data:

| $2\theta$ (°) | d (nm) | I (%) |
|---|---|---|
| 22.7 | 0.391 | 100 |
| 23.0 | 0.386 | 33 |
| 25.1 | 0.354 | 28 |
| 29.0 | 0.307 | 11 |
| 31.3 | 0.285 | 44 |
| 32.9 | 0.272 | 36 |
| 38.4 | 0.232 | 27 |
| 39.6 | 0.227 | 37 |
| 40.2 | 0.224 | 24 |
| 41.6 | 0.217 | 23 |
| 41.7 | 0.216 | 22 |
| 42.4 | 0.213 | 26 |
| 42.6 | 0.212 | 22 |
| 46.0 | 0.197 | 23 |
| 46.1 | 0.197 | 18 |
| 50.1 | 0.182 | 16 |

Wherein:
$\theta$: angle of diffraction
d: lattice plane distance
I: intensity.

EXAMPLE 1a

Preparing catalyst I 400 g of sulfide-free barium carbonate are very vigorously made into a paste at room temperature within 30 minutes using 260 g of 75% aqueous phosphoric acid and then are reacted with further mixing with 90 g of tetrasodiumdiphosphate. The salt paste so formed is then gently dried in a flow of nitrogen in vacuum at about 100° C. over a period of 12 hours.

The salt substance hardened in that manner is mechanically comminuted into irregular fractured particles from 1 to 10 mm and is calcined in nitrogen flow at 550° C. within 24 hours.

The sodium content of the calcined product is 5.2%.

EXAMPLE 2a

Catalyst II 395 g of sulfide-free barium carbonate (from Kali-Chemie Co.) are reacted at room temperature in 17 minutes with 256 g of 76.6% aqueous phosphoric acid solution in a kneader mixer, the temperature rising by 5° to 10° C. After 10 minutes of post-kneading, 183 g of tetrasodiumdiphosphate are added. Kneading continues for another 10 minutes. 720 g of substance are obtained from the kneader (746 g when calculated from the amounts of initial materials).

The mixture is introduced into an extruder (Hutt Mfr) to be shaped. The 4 mm strands so obtained are dried in airflow for 19 hours at 110° C. and then are calcined for 19 hours at 500° C.

| | |
|---|---|
| Loss of mass in drying: | 9.7% |
| Loss of mass in calcining: | 5.8%. |
| Chemical Composition: | |
| BaO content | 47.6% |
| $Na_2O$ content | 11.5 |
| $P_2O_5$ content | 37.0. |
| Physical Properties: | |
| Shape | strands |
| Diameter | 4 mm |
| Length | 2 ... 10 mm |
| Bulk Density | 1.27 g/cm$^3$ |
| Specific Pore Volume | 0.17 cm$^3$/g |
| Specific Inside Surface | 0.8 m$^2$/g |
| Specific Lateral Compressive Strength | 18 +/− 8 N/mm. |

Figure 5:
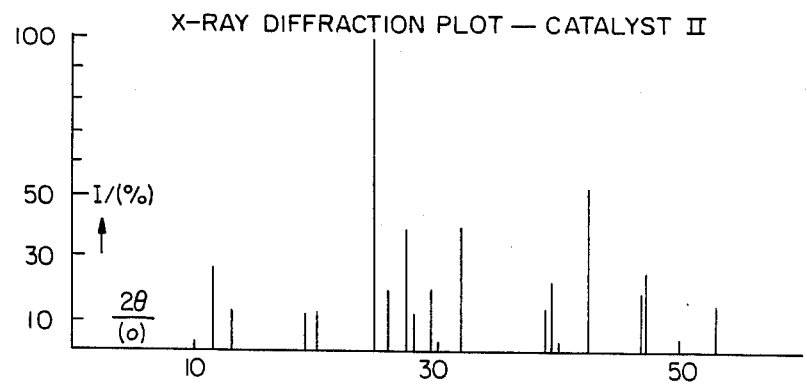
FIG. 5 is a plot of the X-ray diffraction of Catalyst II.

FIG. 5 for catalyst II is based upon the following data:

| 2θ (°) | d (nm) | I (%) |
|---|---|---|
| 11.5 | 1.768 | 27 |
| 13.0 | 1.682 | 12 |
| 19.2 | 1.462 | 12 |
| 20.2 | 1.440 | 13 |
| 25.1 | 1.354 | 100 |
| 28.2 | 1.316 | 12 |
| 26.7 | 1.301 | 20 |
| 32.0 | 1.279 | 40 |
| 38.9 | 1.231 | 13 |
| 39.4 | 1.229 | 21 |
| 42.6 | 1.212 | 53 |
| 46.9 | 1.194 | 19 |
| 47.2 | 1.193 | 25 |
| 52.9 | 1.173 | 14 |

Wherein:
θ: diffraction angle
d: lattice plane distance
I: intensity

EXAMPLE 3a, CATALYST III

Preparation of a dehydration catalyst with the main component being Ba-diphosphate 3,000 g of a sulfide-free barium carbonate (from Kali-Chemie) are reacted in a kneader at a high angular speed of the kneading arms rotating at 81 and 135 rpm at 40° C. with 1,761 g of 84.6% aqueous phosphoric acid solution in 73 minutes. Kneading continues for another 30 minutes, whereupon 555 g of distilled water are added in 27 minutes. Thereupon 1,386 g of tetrasodium-diphosphate are added in one batch and, while kneading, the temperature rapidly rises to 55° C. and then slowly drops. Mixing proceeds for 40 minutes. A powder with much coarser granulates is obtained. The amount obtained is about 5,900 g (calculated amount from the initial materials and subtracting the $CO_2$ generated is 6,033 g).

Water is again added in the ratio of 1:26 to the product for the extrusion procedure and the mixture so obtained is shaped at 50° C. into 4 mm strands. The strands first are dried for 16 hours in an airflow at 110° C. and then are calcined for 4 hours at 450° C.

The material loses about 19% in weight during drying and about 3.7% when calcined.

| Chemical Composition | |
|---|---|
| BaO content | 46.6% |
| SrO content | 0.7 |
| $Na_2O$ content | 13.3 |
| $P_2O_5$ content | 38.8 |
| Structure | |
| X-ray diffraction: (FIG. 7) | $Na_4P_2O_7$ is present; further reflections cannot be ascribed in JCPDS catalog |
| Infra-red absorption (FIG. 8): | absorption bands at 735 $cm^{-1}$ (P-O-P flexure mode vibrations) and at 921 and 956 $cm^{-1}$ (P-O strain mode vibration) indicate diphosphate. |

| Physical Properties | |
|---|---|
| Shape | strands |
| Diameter | 4 mm |
| Bulk Density | 1.69 g/cm³ |
| Specific Pore Volume | |
| (total) | 0.25 cm³/g |
| ($D_p > 56$ nm) | 0.21 cm³/g |
| Specific inside | |
| surface (total) | 3 m²/g |
| ($D_p > 56$ nm) | 1.7 m²/g. |

Figure 7:
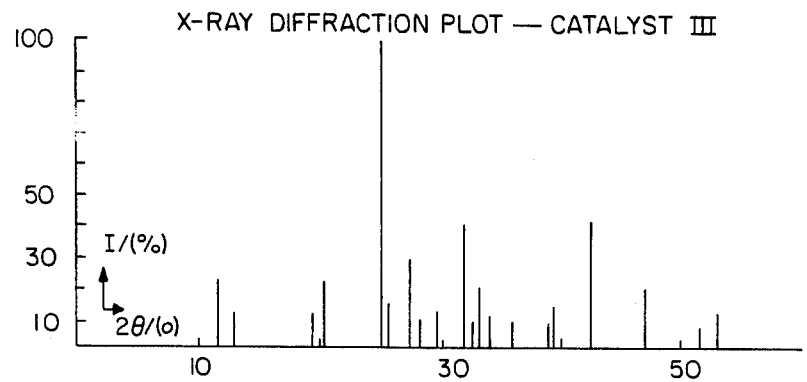
FIG. 7 is a plot of the X-ray diffraction of Catalyst III.

FIG. 7 for catalyst III is based on the following data:

| 2θ (°) | d (nm) | I (%) |
|---|---|---|
| 11.6 | 0.762 | 22 |
| 13.0 | 0.680 | 12 |
| 19.4 | 0.457 | 11 |
| 20.3 | 0.441 | 22 |
| 25.2 | 0.353 | 100 |
| 25.8 | 0.345 | 14 |
| 27.5 | 0.324 | 29 |
| 28.3 | 0.315 | 10 |
| 29.7 | 0.300 | 12 |
| 32.1 | 0.278 | 41 |
| 32.8 | 0.273 | 10 |
| 33.3 | 0.269 | 19 |
| 34.0 | 0.263 | 11 |
| 36.0 | 0.249 | 9 |
| 39.0 | 0.231 | 9 |
| 39.5 | 0.228 | 13 |
| 42.6 | 0.212 | 42 |
| 47.1 | 0.193 | 20 |
| 51.7 | 0.176 | 7 |
| 53.0 | 0.173 | 12. |

Wherein:
θ: diffraction angle
d: lattice plane distance
I: intensity

EXAMPLES 1b, 2b, 3b AND 4 FOR PREPARING THE ALPHA, OMEGA-ENOLS 1 liter of the corresponding catalyst (see following table) is initially introduced into a heatable quartz tube 1 m long and 50 mm in diameter. Adding nitrogen, the particular catalyst is raised to the desired temperature (see table). The temperature is sensed by a resistance thermometer located in a centered quartz tube 6 mm in diameter and axially displaceable therein depending on the need to be moved into the desired position. The molten alpha, omega-alkanediol then is raised by an evaporator with subsequent superheating to the desired reaction temperature and added together with the inert substances to the catalyst. The condensed reactor output is examined by GC and water analysis. These values are corroborated by fractionating the crude product in vacuum. Distillation takes place by means of a 0.5 m Multifil column. After removing the water and the low-boiling point substances at ordinary pressure, the main runnings are isolated at a vacuum of about 10 mbars.

GC stands for gas chromatography
LHSV stands for liquid hourly space velocity

TABLE

| Examples | Educt | Product | Catalyst | Catalyst temperature (°C.) | LHSV ml/ml h | Conversion | Alkanol-content (%) | diene content (%) | Selectivity (%) | Purity (%) |
|---|---|---|---|---|---|---|---|---|---|---|
| Compari- | | | | | | | | | | |

TABLE-continued

| Examples | Educt | Product | Catalyst | Catalyst temperature (°C.) | LHSV ml/ml h | Conversion | Alkanol-content (%) | diene content (%) | Selectivity (%) | Purity (%) |
|---|---|---|---|---|---|---|---|---|---|---|
| son Examples | | | | | | | | | | |
| Examples | | | | | | | | | | |
| A2 | Decanediol | Decenol | A | 430 | 0.30 | 68 | 6.8 | 8.3 | 64.7 | 91.9 |
| B2 | Hexanediol | Hexenol | B | 380 | 0.29 | 94.8 | 0.5 | 11.9 | 49.5 | 84.9 |
| C2 | Hexanediol | Hexenol | C | 400 | 0.45 | 49.1 | 7.4 | 13.5 | 55.0 | 82.7 |
| Examples | | | | | | | | | | |
| 1b | Decanediol | Decenol | I | 400 | 0.45 | 67.8 | 4.4 | 6.9 | 73.5 | 93.2 |
| 2b | Decanediol | Decenol | II | 430 | 0.29 | 94.0 | 0.8 | 5.8 | 84.1 | 95.8 |
| 3b | Decanediol | Decenol | III | 410 | 0.30 | 83.4 | 0.7 | 1.6 | 87.8 | 96.5 |
| 4 | Octanediol | Octenol | II | 420 | 0.29 | 94.9 | 1.4 | 1.9 | 85.8 | 95.4 |
| 5 | Hexanediol | Hexenol | II | 440 | 0.25 | 96.2 | 1.9 | 6.4 | 70.0 | 92.8 |

What we claim is:

1. A method for preparing pure alpha, omega-$C_4$ to $C_{20}$ alkenols having purities in excess of 90% by the catalytic dehydration of the corresponding alpha, omega-$C_4$ to $C_{20}$ diols, comprising:
   (a) reacting an alkaline earth metal compound with phosphoric acid in a paste and forming an alkaline earth metal phosphate reaction product;
   (b) doping said reaction product by adding 2 to 25% by weight of a diphosphate doping compound selected from the group consisting of alkali metal diphosphate and alkaline earth metal diphosphate and forming an alkaline earth metal phosphate reaction product doped with a diphosphate doping compound wherein the percent by weight of said diphosphate doping compound is calculated as metal oxide and referred to the weight of said phosphate reaction product also calculated as metal oxide;
   (c) drying and extruding said phosphate reaction product doped with a diphosphate doping compound and forming a dried and extruded substance;
   (d) calcining said dried and extruded substance at temperatures between 350° to 950° C. to form a catalyst free of diphosphate compound; and
   (e) dehydrating said diols by passing them over said catalyst at temperatures between 300° to 500° C. to form said alkenols having purities in excess of 90% at conversions in excess of 90%.

2. The method of claim 1, wherein said alkaline earth metal compound is barium carbonate.

3. The method of claim 2, wherein said doping compound is tetrasodiumdiphosphate.

4. The method of claim 2 wherein said doping compound is 5 to 15% by weight.

5. The method of claim 4, wherein said temperatures of step (d) are 400° to 600° C.

6. The method of claim 5, wherein said temperatures of step (e) are 350° to 450° C.

7. The method of claim 2, wherein said doping compound is tetracesiumdiphosphate.

8. The method of claim 2, wherein said doping compound is tetrapotassiumdiphosphate.

9. The method of claim 8, wherein said catalyst of step (d) has an infra-red absorption spectrum with strong bands at 920 to 924 $cm^{-1}$ and at 1,126 to 1,130 $cm^{-1}$ and weak bands at 700 to 720 $cm^{-1}$, weak bands at 750 $cm^{-1}$ and weak bands at 1,110 $cm^{-1}$.

10. A method for preparing pure alpha, omega-$C_4$ to $C_{20}$ alkenols having purities in excess of 90% by the catalytic dehydration of the corresponding alpha, omega-$C_4$ to $C_{20}$ diols, comprising:
   (a) reacting barium carbonate with phosphoric acid in a paste and forming a barium phosphate reaction product;
   (b) doping said reaction product by adding 10 to 50% by weight of a diphosphate doping compound selected from the group consisting of tetrasodiumdiphosphate, tetrapotassiumdiphosphate and tetracesiumdiphosphate and forming a barium phosphate reaction product doped with a diphosphate doping compound;
   (c) drying and extruding said barium phosphate reaction product doped with a diphosphate doping compound and forming a dried and extruded substance;
   (d) calcining said dried and extruded substance at temperatures between 350° to 950° C. to form a catalyst having an infra-red absorption spectrum with strong bands at 920 to 924 $cm^{-1}$ and at 1,126 to 1,130 $cm^{-1}$, and weak bands at 700 to 720 $cm^{-1}$ and weak bands at 750 $cm^{-1}$ and weak bands at 1,110 $cm^{-1}$; and
   (e) dehydrating said diols by passing them over said catalyst at temperatures between 300° to 500° C. to form said alkenols having purities in excess of 90% at conversions in excess of 90%.

11. The method of claim 10, wherein said barium carbonate of step (a) is 1 to 10 Kg and said diphosphate doping compound of step (b) is added at the rate of 5 grams to 20 grams per hour.

12. The method of claim 10, wherein said diphosphate doping compound is tetrasodiumdiphosphate.

13. The method of claim 10, wherein said diphosphate doping compound is tetrapotassiumdiphosphate.

14. The method of claim 10, wherein said diphosphate doping compound is tetracesiumdiphosphate.

* * * * *